United States Patent
Tanno

(10) Patent No.: US 11,723,620 B2
(45) Date of Patent: Aug. 15, 2023

(54) RADIOGRAPHIC IMAGING APPARATUS

(71) Applicant: Shimadzu Corporation, Kyoto (JP)

(72) Inventor: Keiichi Tanno, Kyoto (JP)

(73) Assignee: Shimadzu Corporation, Kyoto (KR)

( * ) Notice: Subject to any disclaimer, the term of this patent is extended or adjusted under 35 U.S.C. 154(b) by 190 days.

(21) Appl. No.: 17/495,229

(22) Filed: Oct. 6, 2021

(65) Prior Publication Data

US 2022/0125399 A1     Apr. 28, 2022

(30) Foreign Application Priority Data

Oct. 23, 2020   (JP) .................................. 2020-178210

(51) Int. Cl.
*A61B 6/00*      (2006.01)
*G06F 3/14*      (2006.01)

(52) U.S. Cl.
CPC .............. *A61B 6/542* (2013.01); *A61B 6/461* (2013.01); *G06F 3/14* (2013.01)

(58) Field of Classification Search
CPC ......... A61B 6/542; A61B 6/461; A61B 6/465; A61B 6/54; A61B 6/48; G06F 3/14; G06F 3/147; G09G 2380/08
See application file for complete search history.

(56) References Cited

U.S. PATENT DOCUMENTS

2010/0232573 A1   9/2010 Ozawa et al.
2012/0163534 A1*  6/2012 Nambu ................. A61B 6/487
                                        378/44

FOREIGN PATENT DOCUMENTS

JP     2010213798 A    9/2010
JP     2012019871 A    2/2012

* cited by examiner

*Primary Examiner* — Courtney D Thomas
(74) *Attorney, Agent, or Firm* — Muir Patent Law, PLLC

(57) ABSTRACT

The radiographic imaging apparatus includes a preset setting unit for presetting a dose of X-rays, a standard state setting unit for setting the preset dose as a standard state, and a dose change unit for relatively changing the dose of X-rays from the standard state to at least one of a high-dose state in which the dose of the X-rays is higher than that in the standard state by a predetermined dose and a low-dose state in which the dose of the X-rays is lower than that in the standard state by a predetermined dose.

11 Claims, 4 Drawing Sheets

RADIOGRAPHIC IMAGING APPARATUS

CROSS-REFERENCE TO RELATED APPLICATIONS

The priority application number JP2020-178210, entitled "Radiographic Imaging Apparatus", filed on Oct. 23, 2020, invented by Keiichi TANNO, upon which this patent application is based is hereby incorporated by reference.

BACKGROUND OF THE INVENTION

Field of the Invention

The present invention relates to a radiographic imaging apparatus, and more particularly to a radiographic imaging apparatus for capturing an image of an inside of a body of a subject by irradiating the subject with X-rays.

Description of the Background Art

Conventionally, a cardiovascular X-ray diagnostic apparatus for imaging an inside of a body of a subject by irradiating the subject with X-rays is known. Such an apparatus is disclosed in, for example, Japanese Unexamined Patent Application Publication No. 2010-213798.

The cardiovascular X-ray diagnostic apparatus described in Japanese Unexamined Patent Application Publication No. 2010-213798 can perform imaging by moving the imaging position. This apparatus performs imaging of the lower limb artery from the pelvic area to the foot of the subject by translating the top board, which is a bed for the subject, from the state in which the coronary artery of the heart of the subject being imaged. The coronary arteries and the lower extremity arteries differ in the thickness of the subject, and therefore the imaging program should be changed from the program for a heart to the program for a lower extremity. Therefore, in the cardiovascular X-ray diagnostic apparatus described in Japanese Unexamined Patent Application Publication No. 2010-213798, imaging is performed by changing the imaging program, based on the position information on the imaging position acquired by detecting the position of the top board.

Here, unlike the case where the region of the subject (object) to be imaged is changed as in the case of the cardiovascular X-ray diagnostic apparatus described in Japanese Unexamined Patent Application Publication No. 2010-213798, when X-ray fluoroscopy radiography is performed by irradiating the same region (site) of the subject (subject) with X-rays, there is a case in which the imaging program (imaging condition) for the dose of the X-rays to be emitted while performing the imaging is changed. For example, in a percutaneous coronary intervention (PCI: percutaneous coronary intervention), which is a treatment using a catheter for a coronary stenosis disease, there is a case in which the dose of X-rays to be emitted is increased to improve the visibility of the image to be captured at the timing of, e.g., indwelling a stent at a stenotic site in a blood vessel.

On the other hand, at the timing of, e.g., removing a catheter or the like from an inside of a body of a subject after completion of indwelling of a stent, there is a case in which the dose of X-rays to be emitted is decreased in order to reduce the exposure dose to the subject.

In these cases, an operator, such as, e.g., a doctor, reselects an appropriate specific value of a dose from a plurality of doses (presets) set to correspond to each site of a human body or a manipulation according to the degree of progress of the surgical operation, from the state in which imaging is performed by X-rays of a preset dose. Thus, the imaging condition is changed. However, there is a problem that in a situation where imaging using X-rays of a preset dose is being performed, the task of reselecting an appropriate specific value of a dose from a plurality of preset doses is burdensome for an operator, such as, e.g., a doctor.

SUMMARY OF THE INVENTION

The present invention has been made to solve the above-described problems. One object of the present invention is to provide a radiographic imaging apparatus capable of easily changing a dose of X-rays to be emitted to a subject even in a case where imaging is being performed with X-rays of a dose set in advance for the same region (site).

In order to attain the above-described object, a radiographic imaging apparatus according to one aspect of the present invention relates to a radiographic imaging apparatus for imaging an inside of a body of a subject by emitting X-rays to the subject from an X-ray irradiation unit including an X-ray tube, the radiographic imaging apparatus includes:
  a control unit configured to control X-ray irradiation by the X-ray irradiation unit; and
  an operation unit configured to accept an operation for changing a dose of X-rays to be emitted,
  wherein the control unit includes:
  a preset setting unit configured to preset the dose of X-rays to be emitted;
  a standard state setting unit configured to set the dose of X-rays preset by the preset setting unit as a standard state; and
  a dose change unit configured to relatively change the dose of X-rays to be emitted with the standard state as a reference, based on an operation to the operation unit, from the standard state to at least one of a high-dose state in which the dose of X-rays to be emitted is higher than that in the standard state by a predetermined dose and a low-dose state in which the dose of X-rays to be emitted is lower than that in the standard state by the predetermined dose.

Note that in this specification, the terms "X-ray imaging" and "capturing an X-ray image" are described as a concept including X-ray fluoroscopy (X-ray fluoroscopic imaging) in which X-rays are sequentially (continuously) emitted to a subject.

In the radiographic imaging apparatus according to the above-described one aspect, based on the operation to the operation unit, the dose of X-rays to be emitted is relatively changed, with reference to the standard state, based on an operation to the operation unit, from the standard state to at least one of a high-dose state in which the dose of X-rays to be emitted is higher than that in the standard state by a predetermined dose and a low-dose state in which the dose of X-rays to be emitted is lower than that in the standard state by the predetermined dose. With this, an operator, such as, e.g., a doctor, can relatively change the dose from the dose of the current X-ray irradiation without reselecting an appropriate specific value of a dose from the plurality of doses. Thus, an operator, such as, e.g., a doctor, can easily change the dose of X-rays to be emitted at the appropriate timing by manipulating the operation unit. As a result, an operator, such as, e.g., a doctor, can easily change the dose of X-rays to be emitted to the subject even in a case where imaging is being performed with X-rays of a dose preset for the same region (site).

DESCRIPTION OF THE PREFERRED EMBODIMENT

Hereinafter, some embodiments in which the present invention is embodied will be described with reference to the attached drawings.

Overall Configuration of X-Ray Imaging Apparatus

Referring to FIG. 1 to FIG. 7, an X-ray imaging apparatus 100 according to one embodiment of the present invention will be described. Note that the X-ray imaging apparatus 100 is an example of the "radiographic imaging apparatus" as recited in claims.

Figure 1:
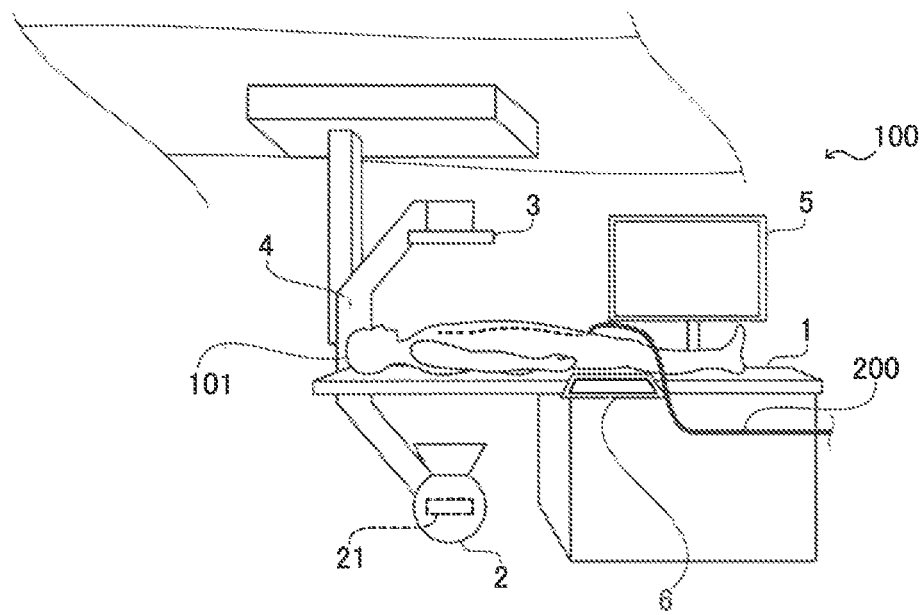
FIG. 1 is a diagram for explaining a configuration of an X-ray imaging apparatus according to one embodiment of the present invention.

As shown in FIG. 1, the X-ray imaging apparatus 100 performs X-ray imaging for capturing images of the inside of the body of the subject 101 by irradiating the subject 101 into which a medical device 200 is inserted. For example, when performing percutaneous coronary intervention (PCI), the X-ray imaging apparatus 100 captures images (moving image) for confirming the inside of the body of the subject 101. The percutaneous coronary intervention is a treatment for resolving stenosis and obstruction of a blood vessel by using the device 200 for angina pectoris and myocardial infarction, which are diseases due to stenosis and obstruction of a coronary artery (coronary arteries) of a heart.

The device 200 is, for example, a catheter to be indwelled in a blood vessel in the vicinity of the heart of the subject 101, a guidewire, or a stent. The device 200 is inserted from a blood vessel (such as, e.g., the radial artery or the femoral artery) of a wrist or a thigh to a stenotic site of a coronary artery. In a percutaneous coronary intervention, the device 200, such as, e.g., a stent inserted into a blood vessel, is placed at the stenotic site of the coronary artery. At the stenotic site of the coronary artery, the stent is expanded to treat the stenosis of the blood vessel.

In the percutaneous coronary intervention, an operator, such as, e.g., a doctor, inserts the device 200, such as, e.g., a stent, into the body of the subject 101 while confirming the internal state of the subject 101 while viewing the X-ray image as a captured moving image.

<X-Ray Imaging Apparatus>

Figure 2:
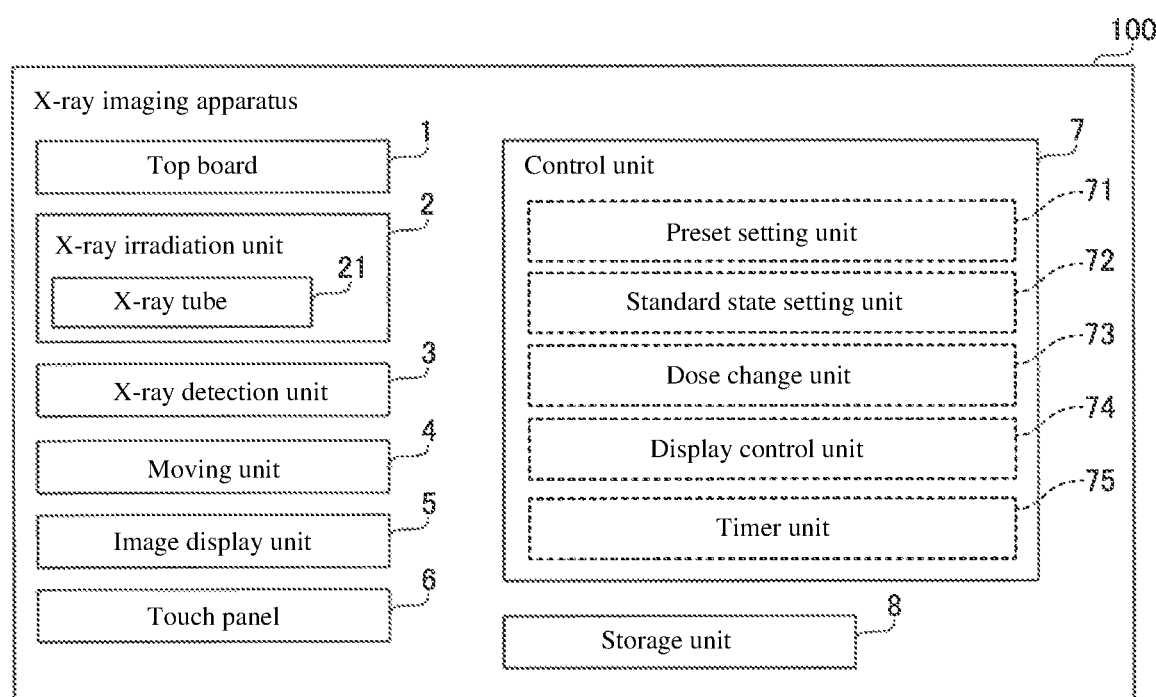
FIG. 2 is a block diagram for explaining a configuration of the X-ray imaging apparatus according to one embodiment.

As shown in FIG. 2, the X-ray imaging apparatus 100 is provided with a top board 1, an X-ray irradiation unit 2, an X-ray detection unit 3, a moving unit 4, an image display unit 5, a touch panel 6, a control unit 7, and a storage unit 8. The X-ray imaging apparatus 100 captures images of the subject 101 by irradiating the subject 101 with X-rays. Specifically, the X-ray imaging apparatus 100 captures X-ray images (X-ray fluoroscopic images) as a moving image. Note that the touch panel 6 is an example of the "operation unit" and the "display unit" recited in claims.

The top board 1 is configured for the subject 101 to lie down thereon. In a state in which the subject 101 lies down on the top board 1, the device 200 is inserted into the subject 101, and X-rays are emitted to capture the images of the inside of the body. The top board 1 is configured to be movable by a top board moving unit (not shown).

The X-ray irradiation unit 2 irradiates the subject 101 with X-rays. The X-ray irradiation unit 2 includes an X-ray tube 21 which emits X-rays when a voltage is applied. The X-ray tube 21 is configured such that the X-rays to be emitted is controlled when the voltage and the current applied to the X-ray tube 21 is controlled by the control unit 7. Further, in this embodiment, the X-ray irradiation unit 2 is configured to continuously emit X-rays to capture X-ray images of the subject 101 as a moving image.

The X-ray detection unit 3 detects the X-rays transmitted through the subject 101. The X-ray detection unit 3 outputs a detection signal based on the detected X-rays. The X-ray detection unit 3 includes, for example, an FPD (flat panel detector). The X-ray detection unit 3 outputs a detection signal for generating X-ray images as a moving image by detecting the X-rays continuously emitted by the X-ray irradiation unit 2.

The moving unit 4 holds the X-ray irradiation unit 2 and the X-ray detection unit 3 in a moveable manner. Specifically, the moving unit 4 supports the X-ray irradiation unit 2 and the X-ray detection unit 3 so as to oppose each other with the top board 1 on which the subject 101 lies interposed therebetween. The moving unit 4 supports the X-ray irradiation unit 2 and the X-ray detection unit 3 such that the position and the angle of the X-ray irradiation unit 2 and the X-ray detection unit 3 with respect to the subject 101 can be changed. The moving unit 4 supports the X-ray irradiation unit 2 and the X-ray detection unit 3 such that the position and the angle of the X-ray irradiation unit 2 and the X-ray detection unit 3 with respect to the subject 101 can be changed. Further, the moving unit 4 includes, for example, a servo motor. The moving unit 4 moves the X-ray irradiation unit 2 and the X-ray detection unit 3 in order to perform X-ray imaging with respect to the subject 101 at various positions and various angles.

The image display unit 5 is a monitor, such as, e.g., a liquid crystal display. Further, the image display unit 5 displays the captured X-ray image (still image and moving image). Specifically, the image display unit 5 displays the X-ray image generated based on the detection signal detected by the X-ray detection unit 3.

The touch panel 6 is configured to accept an input operation for operating the X-ray imaging apparatus 100 by an operator, such as, e.g. a doctor. More specifically, in this embodiment, the touch panel 6 accepts an operation for changing the dose of the X-rays emitted by the X-ray irradiation unit 2. Further, the touch panel 6 receives an input operation for executing the control by the control unit 7. Further, the touch panel 6 displays, based on the control by the control unit 7 (display control unit 74) to be described later, the information about the dose of X-rays emitted from the X-ray irradiation unit 2. The touch panel 6 is provided at the top board 1. The operations to the touch panel 6 and the indication on the touch panel 6 will be described in detail later.

The control unit 7 includes, for example, an FPGA (field-programmable gate array). The control unit 7 performs a predetermined control program to control the X-ray irradiation by the X-ray irradiation unit 2. The control unit 7 includes, as functional components, a preset setting unit 71, a standard state setting unit 72, a dose change unit 73, a display control unit 74, and a timer unit 75. That is, the control unit 7 functions as the preset setting unit 71, the standard state setting unit 72, the dose change unit 73, the display control unit 74, and the timer unit 75 by executing predetermined control programs.

The preset setting unit 71, the standard state setting unit 72, the dose change unit 73, the display control unit 74, and the timer unit 75 are software functional blocks in the control unit 7 and are configured to function based on the command signal of the control unit 7 as hardware. The details of the control by the control unit 7 will be described later.

The storage unit 8 is configured by a storage device, such as, e.g., a hard disk drive. In this embodiment, the storage unit 8 stores a plurality of doses set so as to correspond to a surgical operation to be performed on the subject 101. That is, the storage unit 8 stores a plurality of presets set so as to correspond to a surgical operation to be performed on the subject 101. Further, the storage unit 8 is configured to store images data and various set values.

(Presets)

Figure 3:
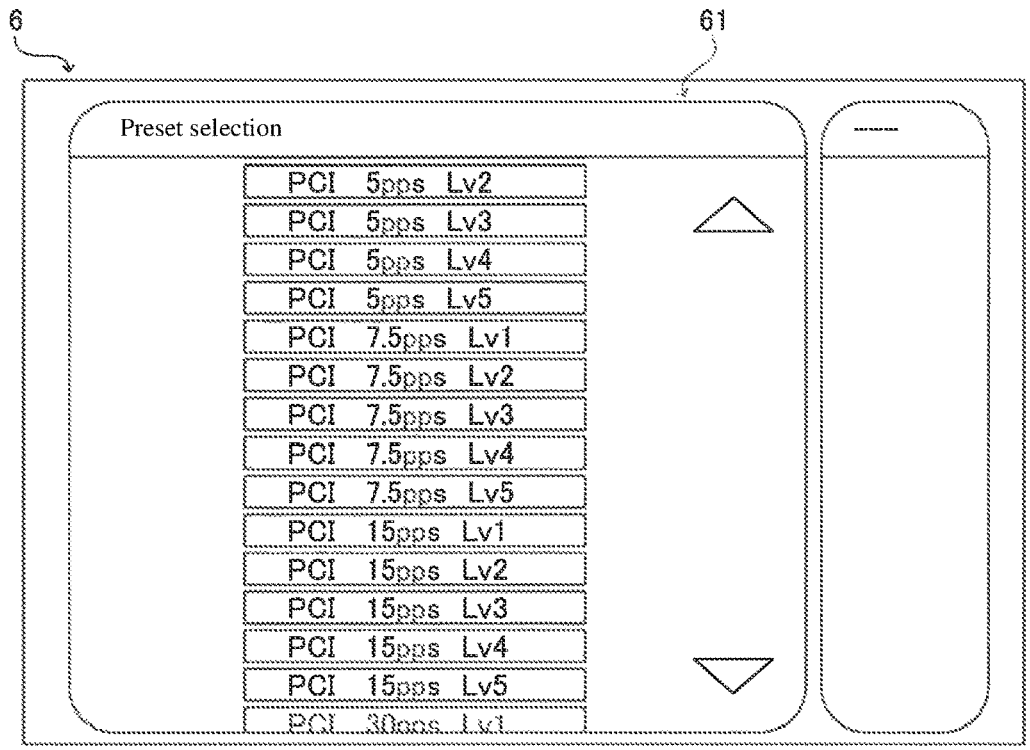
FIG. 3 is a diagram for explaining a selection of a preset according to one embodiment.

As shown in FIG. 3, the X-ray imaging apparatus 100 is configured to perform imaging based on a set preset (dose). Specifically, the X-ray imaging apparatus 100 controls the pulse rate and the pulse dose of the X-rays continuously emitted based on the set preset. The pulse rate denotes the number times of X-ray irradiations per second (unit time). The pulse dose denotes a dose of X-rays emitted by a single irradiation. The pulse rate and the pulse dose each are set to a predetermined value by controlling the magnitude and the pulse-width of the current and the voltage applied to the X-ray tube 21 of the X-ray irradiation unit 2.

The pulse dose of X-rays to be emitted is automatically adjusted based on the dose of the X-rays detected by the X-ray detection unit 3. Here, even in a case where X-rays of the same dose are emitted, the magnitude of the dose of the detected X-rays changes due to the differences in the size and the orientation of the subject 101. Therefore, the voltage and the current applied to the X-ray tube 21 are controlled such that the dose of the X-rays detected by the X-ray detection unit 3 falls within a predetermined range. That is, in accordance with the set preset, the pulse dose of X-rays to be emitted is controlled such that the image quality (brightness, contrast, etc.) of the X-ray image to be captured falls within a predetermined range.

For example, in a case where the "pulse rate: 7.5 pps, the pulse dose: Lv3" is set as a preset, X-rays are emitted at intervals of 7.5 times per second, and the dose of X-rays to be emitted is controlled such that the dose of the X-rays (the strength of the signal output from the X-ray detection unit 3) detected by the X-ray detection unit 3 becomes a magnitude corresponding to the "pulse dose: Lv3".

Further, in a case where the "pulse rate: 7.5 pps, the pulse dose: Lv2" is set as a preset, in the same manner as described above, X-rays are emitted at the intervals of 7.5 per second and the dose of X-rays to be emitted is controlled such that the dose (the strength of the signal output from the X-ray detection unit 3) detected by the X-ray detection unit corresponds to the "pulse dose: Lv2" which is relatively smaller than the "pulse dose: Lv3".

Further, in a case where the "pulse rate: 15 pps, the pulse dose: Lv4" is set as a preset, X-rays are emitted at the intervals of 15 times per second, and the dose of X-rays (the strength of the signal output from the X-ray detection unit 3) detected by the X-ray detection unit 3 becomes larger than the "pulse dose: Lv3".

When the pulse rate (pps: pulse per second) is large, the moving image of the X-ray image to be captured becomes smooth, and when the pulse dose is large, the visibility of the X-ray image to be captured is improved. Prior to a surgical operation, an operator, such as, e.g., a doctor, selects an appropriate preset from a plurality of doses (presets) stored in advance in the storage unit 8 in accordance with the type of the surgical operation (manipulation) to be performed on the subject 101, the size, age, and condition of the subject 101, and the like such that the X-ray image to be captured can be appropriately displayed.

For example, the touch panel 6 displays a preset selection window 61 based on the operation on the touch panel 6 before performing X-ray imaging (before the surgical operation). The preset selection window 61 selectable displays a plurality of presets stored in the storage unit 8 in advance. An operator, such as, e.g., a doctor, selects an appropriate preset to be used for capturing an X-ray image among the plurality presets displayed on the touch panel 6 by performing a selection operation on the touch panel 6.

In this embodiment, the preset setting unit 71 (control unit 7) presets the dose of X-rays to be emitted. More specifically, the preset setting unit 71 is configured to set the dose selected from a plurality of doses (presets) as a dose of X-rays to be emitted. The preset setting unit 71 is configured to preset the dose of X-rays to be emitted prior to the surgical operation to be performed while imaging the subject 101. That is, the preset setting unit 71 sets the dose (pulse rate and pulse dose) of the X-ray irradiation so as to correspond to the selected preset, based on the selection operation of selecting the preset with respect to the touch panel 6.

In the X-ray imaging apparatus 100 according to this embodiment, the X-ray imaging is started by continuously emitting the X-rays of the dose (pulse rate and pulse dose) of the preset set by the preset setting unit 71, based on the operation for the imaging start button (not shown).

(Relative Changes in Dose)

The X-ray imaging apparatus 100 according to this embodiment relatively changes the dose (pulse rate and pulse dose) of X-rays during the X-ray imaging (during the surgical operation) by successive X-ray irradiation, based on the operation for the touch panel 6.

<Setting of Standard State>

In this embodiment, the standard state setting unit 72 (control unit 7) sets the dose preset by the preset setting unit 71 as a standard state. Specifically, the standard state setting unit 72 is configured to set, as a standard state, the dose preset by the preset setting unit 71 before imaging from a plurality of doses stored in the storage unit 8.

That is, the standard state setting unit 72 sets the preset selected from the plurality of presets as a standard state to be a reference. Specifically, the standard state setting unit 72 sets the dose (pulse rate and pulse dose) of the preset set by the preset setting unit 71 as a standard state to be a reference.

<Changing in Dose>

In this embodiment, the dose change unit 73 (control unit 7) is configured to relatively change the dose of X-rays to be emitted from the standard state to the high-dose state or the low-dose state, based on the input operation to the touch panel 6 during the surgical operation performed while imaging the subject 101.

The high-dose state is a state in which the dose of X-rays to be emitted is higher than that in the standard state by a predetermined dose. That is, the high-dose state is a state in which at least one of the pulse rate and the pulse dose is higher than that in the standard state by a predetermined dose. The low-dose state is a state in which the dose of X-rays to be emitted is lower than that in the standard state by a predetermined dose.

In other words, the low-dose state is a state in which at least one of the pulse rate and the pulse dose is lower than that in the standard state by a predetermined dose. The dose change unit 73 is configured to change the dose of X-rays to be emitted from the standard state to the high-dose state or the low-dose state by relatively changing at least one of the pulse rate and the pulse dose from the set standard state by a predetermined dose.

The X-ray imaging apparatus 100 is configured to be able to select a pulse rate as a preset to the values of, for example, 1, 2, 3, 5, 7.5, 15, and 30 pps. The dose change unit 73 changes the pulse rate set as the standard state to any pulse rate among the plurality of pulse rates that can be set by the X-ray imaging apparatus 100.

For example, in a case where the pulse rate in the standard state is set to 7.5 pps, the dose change unit 73 changes the dose from the standard state to the high-dose state by changing the pulse rate from 7.5 to 15 or 30. The dose change unit 73 changes from the standard state to the low-dose state by changing the pulse rate from 7.5 to 1, 2, 3, or 5.

Note that it may be configured such that the pulse rate can be set to another value (e.g., 10 or the like). It may be configured such that the pulse rate can be set by an abstract expression, such as, e.g., "High" and "Low", instead of specific numerical values.

The X-ray imaging apparatus 100 is configured such that, for example, the pulse dose can be selected as a preset at five levels of Lv1 to Lv5. The pulse dose Lv1 is the smallest dose and the pulse dose Lv5 is the largest dose, as a dose per pulse. Note that it may be configured such that the pulse can be changed to more than five levels or to less than 5 levels. Note that the pulse dose may be configured to be settable by expressions such as, e.g., "High" and "Low", or may be configured to be settable by a specific numerical value.

In this embodiment, the dose change unit 73 (control unit 7) is configured to relatively change the dose of X-rays to be emitted from the standard state to levels smaller in the number than the number of levels of the plurality of doses (presets) stored in the storage unit 8. The dose change unit 73 is configured to relatively change the dose of X-rays to be emitted from the standard state to a smaller number of levels than the number of dose types (preset types) selectable as a preset.

Specifically, the dose change unit 73 is configured to relatively change the pulse dose from the standard state to a high-dose state in which the pulse dose is set to a level higher than the level of the standard state by one level and a low-dose state in which the pulse dose is set to a level lower than the level of the standard state by one level. That is, the dose change unit 73 is configured to be able to change the pulse dose to a high-dose state which is increased by one level from the level of the standard state and a low-dose state which is decreased by one level from the level of the standard state.

For example, when the pulse dose of Lv3 is set as a standard state, the dose change unit 73 changes the dose from the standard state to a high-dose state by changing the pulse dose of Lv3 to the pulse dose of Lv4. When the pulse dose of Lv3 is set as a standard state, the dose change unit 73 changes the dose from the standard state to the low-dose state by changing the pulse dose of Lv3 to the pulse dose of Lv2. In other words, even in a case where five types of pulse doses can be selected as presets, the dose change unit 73 can be changed to only two types of pulse doses with the standard state as a reference.

<Displaying and Operating Touch Panel>

Figure 4:
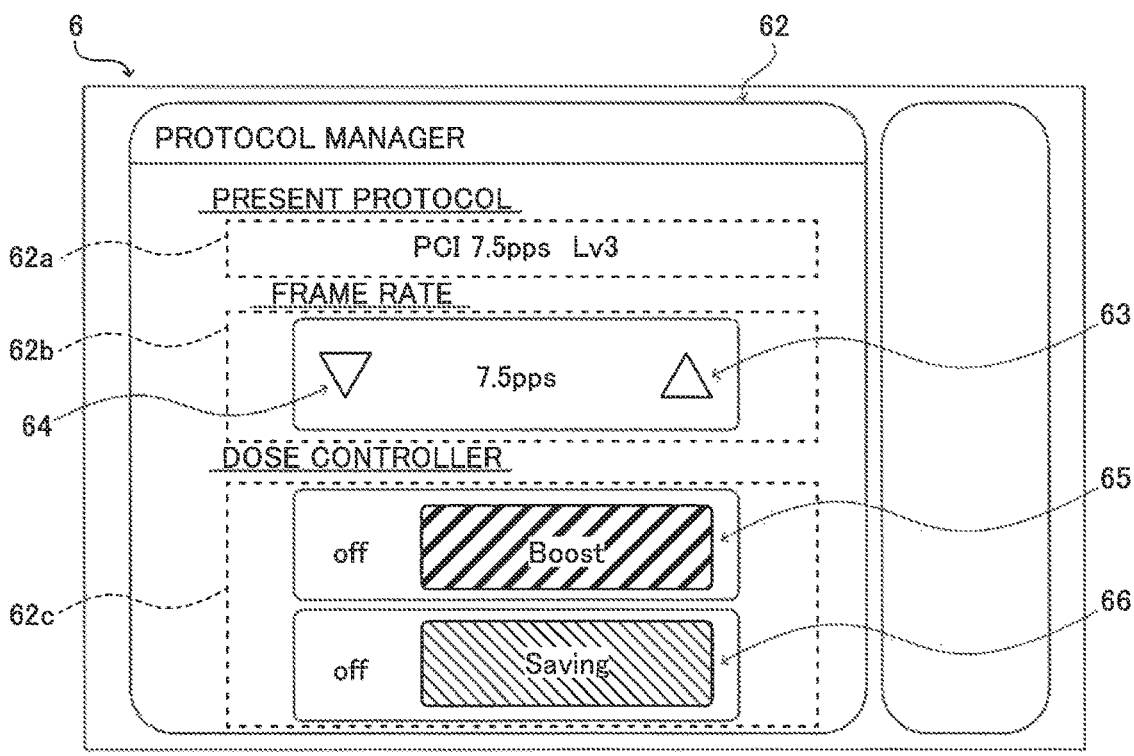
FIG. 4 is a diagram for explaining a touch panel display according to one embodiment.

As shown in FIG. 4, the display control unit 74 (control unit 7) causes the touch panel 6 to display a dose change screen 62 for relatively changing the dose of X-rays to be emitted. In this embodiment, the touch panel 6 includes a button for changing the pulse rate and a button for changing the pulse dose. That is, the display control unit 74 causes the touch panel 6 to display a button for changing the pulse rate and a button for changing the pulse dose. Note that the display control unit 74 makes the touch panel 6 keep displaying the dose change screen 62 when X-ray imaging is being performed.

The display control unit 74 causes the touch panel 6 to display an indication capable of identifying the dose (preset) as a standard state on the region 62a of the dose change screen 62 of the touch panel 6. Specifically, the display control unit 74 causes the touch panel 6 to display the name of the dose (preset) set as a standard state in the region 62a as character information so as to be identifiable. Note that it may be configured such that the display control unit 74 causes the touch panel 6 to display the pulse rate and the pulse dose in a standard state as character information.

Further, the display control unit 74 causes the touch panel 6 to display the pulse rate of the X-ray irradiation in an identifiable manner in the region 62b of the dose change screen 62 of the touch panel 6. Specifically, the display control unit 74 causes the touch panel 6 to display character information indicating the specific value of the pulse rate in the region 62b. The display control unit 74 causes the touch panel 6 to display the rate change buttons 63 and 64 in the region 62b as buttons for changing pulse rates.

The touch panel 6 accepts an input operation for changing the pulse rate when an operator, such as, e.g., a doctor, operates the rate change buttons 63 and 64 in the region 62b. Further, the display control unit 74 is configured to cause the touch panel 6 to display the changed pulse rate value (e.g., 15 pps in FIG. 7) in the region 62b when the pulse rate has been changed.

The display control unit 74 causes the touch panel 6 to display a "Boost" button 65 and a "Saving" button 66 in the region 62c as a button for changing the pulse dose. The touch panel 6 accepts an input operation for changing the pulse dose when an operator, such as, e.g., a doctor, operates the "Boost" button 65 and the "Saving" button 66 in the region 62c.

That is, the touch panel 6 accepts an operation for relatively increasing the pulse dose from the standard state, based on the operation to the "Boost" button 65. The touch panel 6 accepts an operation for relatively decreasing the pulse dose from the standard state, based on the operation to the "Saving" button 66. In a state where neither the "Boost" button 65 nor the "Saving" button 66 is operated in the standard state, the display control unit 74 causes the touch panel 6 to display "off" next to each of the "Boost" button 65 and the "Saving" button 66 to indicate that the pulse dose has not been changed from the standard state.

Figure 5:
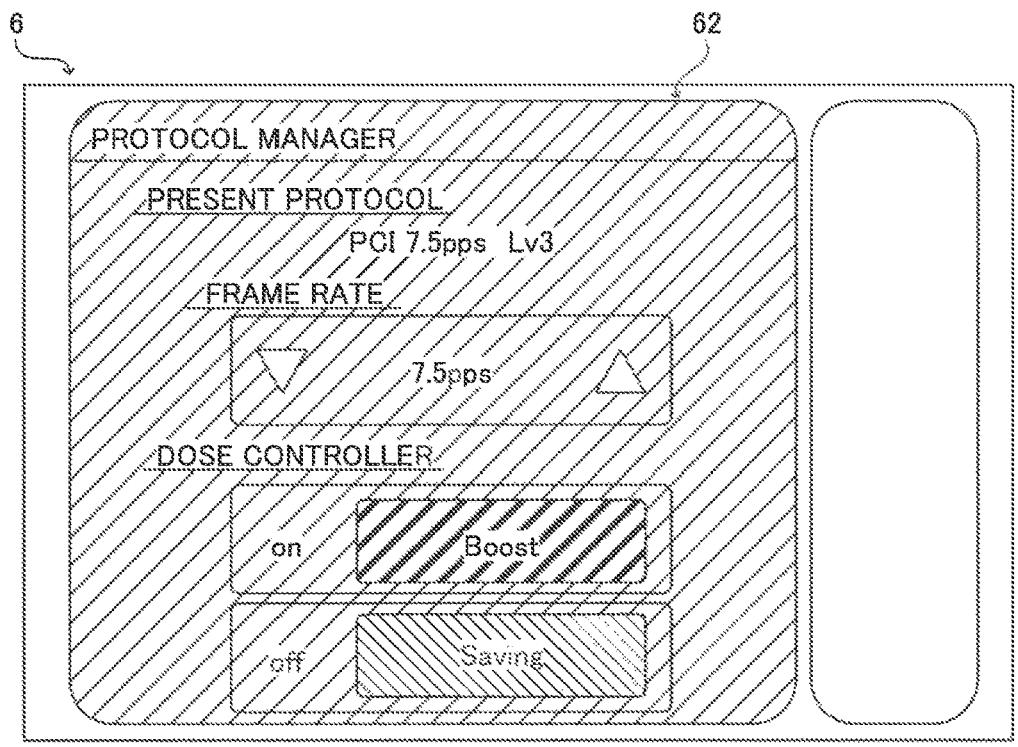
FIG. 5 is a diagram for explaining an indication of a touch panel in a high-dose state according to one embodiment.
Figure 6:
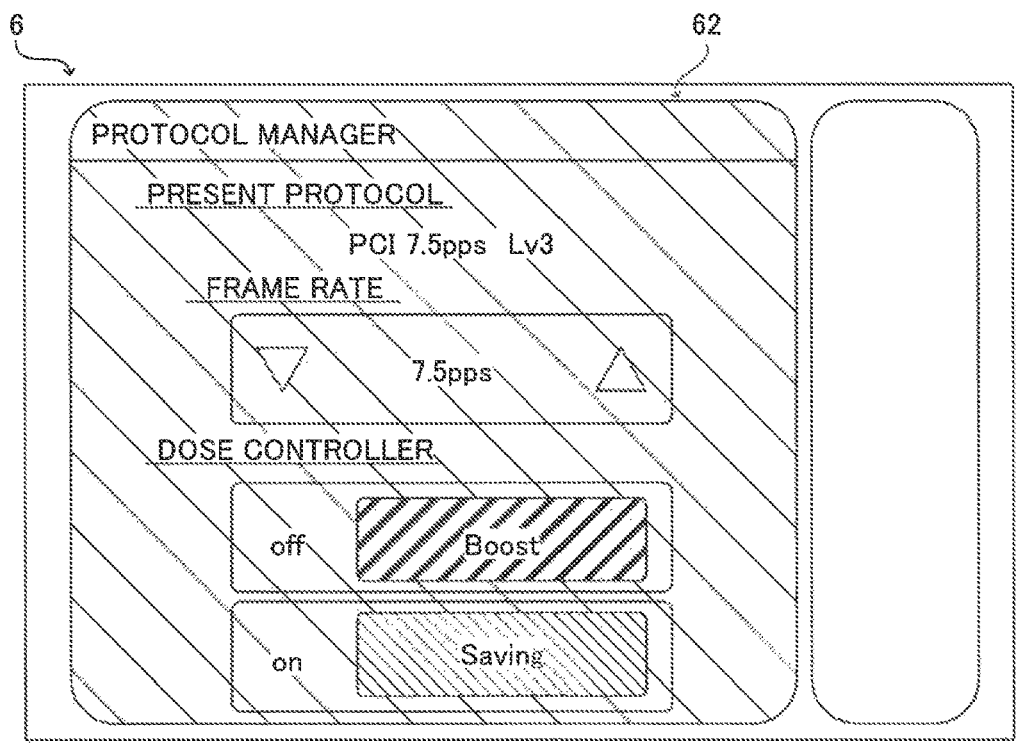
FIG. 6 is a diagram for explaining an indication of a touch panel in a low-dose state according to one embodiment.

As shown in FIGS. 5 and 6, in this embodiment, the display control unit 74 (control unit 7) causes the touch panel 6 to display a visually identifiable display indicating whether or not each of the pulse rate and the pulse dose has been changed from the standard state. That is, in this embodiment, the touch panel 6 displays the standard state, the high-dose state, and the low-dose state in an identifiable manner. Specifically, the display control unit 74 is configured to cause the touch panel 6 to display the standard state, the high-dose state, and the low-dose state in a color-coded manner.

As shown in FIG. 5, in a state in which the X-rays of a dose in the high-dose state are being emitted, the display control unit 74 changes the background color of the display (dose change screen 62) of the touch panel 6 to red. As shown in FIG. 6, in a state in which the X-rays of the dose in the low-dose state are being emitted, the display control unit 74 changes the background color of the dose change screen 62 of the touch panel 6 to green.

Note that when the dose is changed so as to increase at least one of the pulse rate and the pulse dose, the display control unit 74 changes the background color of the dose change screen 62 to red on the assumption that the dose has been changed from the standard state to the high-dose state. When the dose is changed to reduce at least one of the pulse rate and the pulse dose, the display control unit 74 changes the background color of the dose change screen 62 to green, assuming that the standard state has been changed to the low-dose state. Note that in FIGS. 5 and 6, the color-coding is represented by hatching.

Further, the display control unit 74 changes the indication next to the "Boost" button 65 from "off" to "on" when the irradiation is performed by relatively increasing the pulse dose from the standard state by operating the "Boost" button 65. Further, the display control unit 74 changes the indication next to the "Saving" button 66 from "off" to "on" when the irradiation is performed by relatively decreasing the pulse dose from the standard state by operating the "Saving" button 66. As described above, the display control unit 74 displays whether or not the pulse dose has been changed from the standard state in an identifiable manner by character information.

Further, the dose change unit 73 is configured to change (restore) the dose of X-rays to be emitted to the standard state set by the standard state setting unit 72 from the state in which the X-ray irradiation in the high-dose state or low-dose state is being performed, based on the input operation to the touch panel 6.

For example, in a state in which the X-ray irradiation is being performed in a state in which the pulse dose has been relatively increased from the standard state in accordance with the operation of the "Boost" button 65, when the operation to the "Boost" button 65 is performed again, the pulse dose is changed to the standard state. Similarly, in a state in which the X-ray irradiation is being performed in a state in which the pulse dose has been relatively decreased from the standard state in accordance with the operation of the "Saving" button, when the operation to the "Boost" button 65 is performed again, the pulse dose is changed to the standard state.

Further, the dose change unit 73 is configured to be able to change the dose of X-rays to be emitted to the high-dose state from the state in which the X-ray irradiation of a dose in the low-dose state is being performed. Further, the dose change unit 73 is configured to be able to change the dose of X-rays to be emitted to the low-dose state from the state in which the X-ray irradiation of a dose in the high-dose state is being performed. For example, when an operation to the "Saving" button 66 is performed in a state in which the X-ray irradiation is being performed by relatively increasing the pulse dose from the standard state in accordance with the operation to the "Boost" button 65, the pulse dose is changed to a relatively low pulse dose (low-dose state) as compared with the standard state.

(Control when High-Dose State has Continued for Certain Period of Time)

The timer unit 75 (control unit 7) acquires the time information by measuring time. Specifically, when the dose of X-rays to be emitted is changed from the standard state to the high-dose state by the dose change unit 73, the timer unit 75 measures the time from the timing at which the dose is changed to the high-dose state. Then, the timer unit 75 acquires the time information indicating that the X-ray radiation in the high-dose state has continued for a predetermined period of time or longer when a predetermined period of time (e.g., one minute) has elapsed from the timing at which the dose was changed to the high-dose state.

Figure 7:
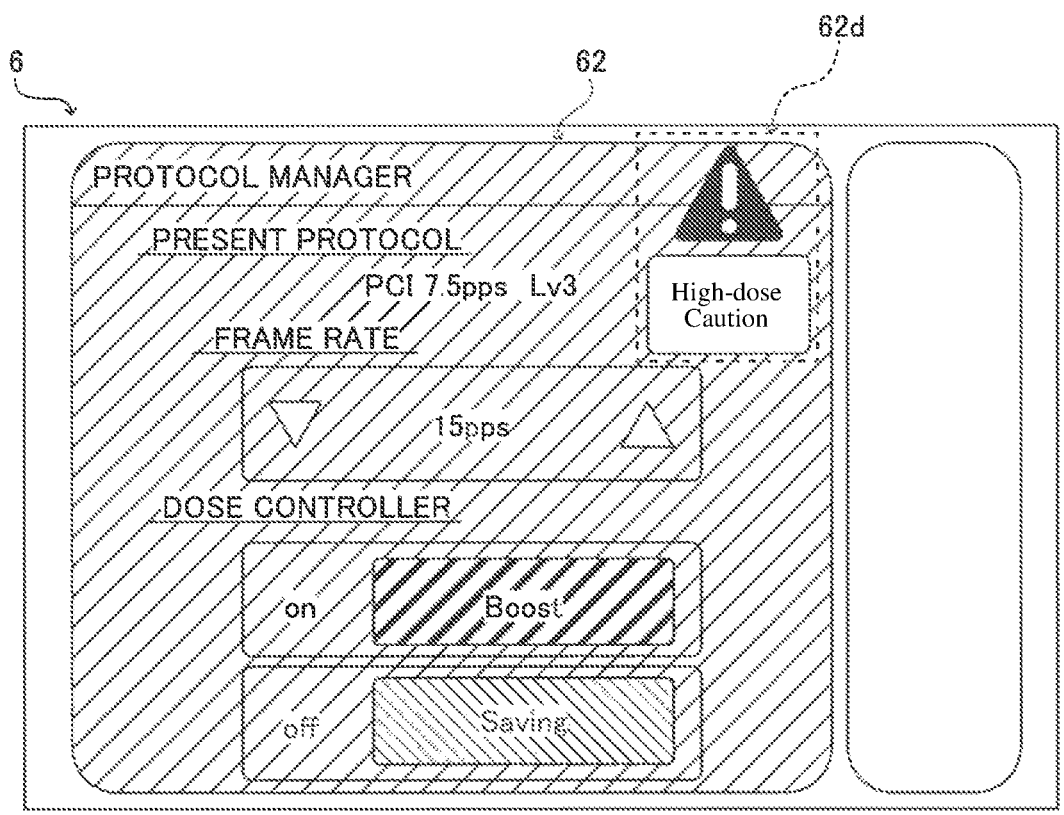
FIG. 7 is a diagram for explaining an indication of a touch panel when a high-dose state has continued for a certain time or more according to one embodiment.

As shown in FIG. 7, in this embodiment, the display control unit 74 (control unit 7) is configured to display, on the touch panel 6, an indication for notifying that the X-ray irradiation in the high-dose state has continued for a predetermined period of time or longer when the X-ray irradiation in the high-dose state has continued for a predetermined period of time or longer.

For example, the display control unit 74 causes the touch panel 6 to display the indication indicating that the high-dose state has continued for a predetermined period of time or longer in the region 62d of the touch panel 6, based on the time information from the timer unit 75. The display control unit 74 causes the touch panel 6 to display the indication notifying that the high-dose state has continued for a predetermined period of time or longer, by displaying the indication by character information and the indication by a mark (symbol) together in the region 62d of the touch panel 6.

Further, the dose change unit 73 (control unit 7) is configured to change the X-ray irradiation to the standard state when the X-ray irradiation in the high-dose state has continued for a predetermined period of time or longer. In other words, the dose change unit 73 changes the dose from the high-dose state to the standard state based on the time information from the timer unit 75.

That is, the X-ray imaging apparatus 100 according to this embodiment is configured to automatically change the dose of X-rays to be emitted to the standard state from the high-dose state while displaying the indication that the high-dose state has continued when the X-ray irradiation in the high-dose state has continued for a predetermined period of time (1 minute) or longer.

Effects of this Embodiment

In this embodiment, the following effects can be obtained.

In the X-ray imaging apparatus 100 of this embodiment, as described above, based on the operation to the touch panel 6 (operation unit), the dose of X-rays to be emitted is relatively changed from the standard state to at least one of the high-dose state in which the dose is higher than that in the standard state by a predetermined dose and the low-dose state in which the dose of X-rays to be emitted is lower than that in the standard state by a predetermined operation unit, based on the operation to the touch panel (operation unit) with the standard state as a reference.

With this, an operator, such as, e.g., a doctor, can relatively change the dose from the dose of the current X-ray irradiation, without reselecting an appropriate specific value of the dose from a plurality of doses. Therefore, an operator, such as, e.g., a doctor, can easily change the dose of X-rays to be emitted at an appropriate timing by operating the touch panel 6. As a result, an operator, such as, e.g., a doctor, can easily change the dose of X-rays to be emitted to the subject 101 even in the case where imaging is being performed by the X-rays of a dose set in advance for the same region (site).

Further, in the above-described embodiment, the following effects can be further acquired by the following configuration.

That is, in this embodiment, as described above, the X-ray irradiation unit 2 is configured to continuously emit X-rays to capture an image of the inside of the body of the subject 101 as a moving image. The dose change unit 73 (control unit 7) is configured to change the dose of X-rays to be emitted, from the standard state to the high-dose state or the low-dose state by relatively changing at least one of the pulse rate, which is the number of times of irradiation of X-rays emitted per unit time and the pulse dose, which is the dose of the X-rays emitted by one irradiation, by a predetermined dose from the set standard state.

With this configuration, it is possible to easily change the number of display images of the captured moving image per second by changing the pulse rate from the standard state by a predetermined dose, and also possible to easily change the visibility of the moving image to be captured by changing the pulse dose from the standard state by a predetermined dose. Therefore, according to the degree of progress of the surgical operation, it is possible to easily switch between the state in which the smoothness and visibility of the image to be displayed are improved although the exposure dose is increased and the state in which the exposure dose is reduced even although the smoothness and visibility of the image to be displayed are decreased. As a result, it is possible to easily improve the moving image display only when a complicated manipulation is required in accordance with the degree of progress of the surgical operation. Therefore, it is possible to easily suppress unnecessary irradiation with a high dose.

In this embodiment, as described above, the preset setting unit 71 (control unit 7) is configured to preset the dose of X-rays to be emitted before performing the surgical operation while imaging the subject 101, and the dose change unit 73 (control unit 7) is configured to change the dose of X-rays to be emitted from the standard state to the high-dose state or the low-dose state, based on the input operation to the touch panel 6 (operation unit) during a surgical operation while imaging three subject 101.

With this configuration, the dose of X-rays to be emitted can be easily changed by operating the touch panel 6 even during the surgical operation. Therefore, without hindering the progress of the surgical operation, it is possible to easily switch between improving the visibility of the captured image and suppressing the increase of the exposure dose.

In this embodiment, as described above, the preset setting unit 71 (control unit 7) is configured to set the dose selected from a plurality of doses as a dose of X-rays to be emitted. Further, the dose change unit 73 (control unit 7) is configured to relatively change the dose of X-rays to be emitted from the standard state to one of numbers of levels fewer than the numbers of a plurality of levels of the doses.

With this configuration, as compared with the case in which one dose is selected from a plurality of doses for setting a preset, in a case where the dose of X-rays to be emitted is changed by the dose change unit 73, the dose can be set from among smaller options. Therefore, when the dose of X-rays to be emitted is changed by the dose change unit 73, it is possible to suppress an increase in the labor of determining the option to be changed by an operator, such as, e.g., a doctor, due to too many options. As a result, by reducing the options, the operator, such as, e.g., a doctor, can easily select the dose of X-rays to be emitted.

Also, in this embodiment, as described above, the dose change unit 73 (control unit 7) is configured to relatively change the pulse dose from the standard state to the high-dose state set to a level higher than the standard state by one level or the low-dose state set to a level lower than the standard state by one level.

With this configuration, the operator, such as, e.g., a doctor, can select the dose to be changed from two options: a level that is higher than the standard state by one level and a level that is lower than the standard state by one level. Therefore, the operator, such as, e.g., a doctor, can more easily select the dose of X-rays to be emitted.

Further, in the embodiment, as described above, it is further provided with a touch panel 6 (display unit) capable of distinguishably displaying the standard state, the high-dose state, and the low-dose state, as described above, and the control unit 7 is provided with a display control unit 74 for displaying, on the touch panel 6, a visually distinguishable indication indicating whether or not each of the pulse rate and the pulse dose has been changed from the standard state.

With this configuration, the standard state, the high-dose state, and the low-dose state can be visually distinguished easily by visually recognizing the touch panel 6. Therefore, since the magnitude of the dose of the X-ray which is being emitted can be easily recognized, it is possible to suppress the subject 101 from being irradiated with a dose more than required.

Further, in this embodiment, as described above, the display control unit 74 (control unit 7) is configured to display the standard state, the high-dose state, and the low-dose state in a color-coded manner on the touch panel 6 (display unit).

With this configuration, the standard state, the high-dose state, and the low-dose state can be visually distinguished more easily by visually recognizing the color-coded touch panel 6. Therefore, since the magnitude of the dose of the X-ray which is being irradiated can be more easily recognized, it is possible to further suppress the subject 101 from being irradiated with a dose more than required.

In this embodiment, as described above, the top board 1 on which a subject 101 lies down is further provided, and the touch panel 6 (operation unit) is provided to the top board 1 and includes a button for changing the pulse rate and a button for changing the pulse dose.

With this configuration, the pulse rate and the pulse dose can be easily changed by operating the touch panel 6 provided on the top board 1 on which the subject 101 lies down. Therefore, when a surgical operation is performed on the subject 101 lying down on the top board 1, since there is no need for the operator to move to a position distanced away from the subject 101 in order to operate the touch panel 6, the pulse rate and the pulse dose can be easily changed while performing the surgical operation.

In addition, in this embodiment, as described above, it is further provided with the storage unit 8 for storing a plurality of doses set so as to correspond to the surgical operation to be performed on the subject 101. The standard state setting unit 72 (control unit 7) is configured to set, as a standard state, the dose preset by the preset setting unit 71 (control unit 7) from a plurality of doses stored in the storage unit 8 before imaging. The display control unit 74 is configured to cause the touch panel 6 (display unit) to display an indication that the doses preset by the preset setting unit 71 can be identifiable.

With this configuration, the preset selected from the plurality of presets (X-ray doses) stored in advance can be easily identified by visually recognizing the display of the touch panel 6. Therefore, by identifying the selected preset, the status of the dose set as a standard state can be identified. For this reason, it is possible to easily recognize the dose of the X-rays which are being emitted to the subject 101.

Further, in this embodiment, as described above, the display control unit 74 (control unit 7) is configured to display, on the touch panel 6 (display unit), the indication notifying that the X-ray irradiation in the high-dose state has continued for a certain period of time or longer when the X-ray irradiation in the high-dose state has continued for a certain period of time or longer.

With this configuration, it can be easily recognized that the X-ray irradiation of a relatively high dose in the high-dose state has continued. Therefore, it is possible to suppress the sum of doses of the X-rays emitted to the subject 101 from becoming excessive.

In this embodiment, as described above, the dose change unit 73 (control unit 7) is configured to change the dose of the X-rays to be emitted to the standard state when the X-ray irradiation in the high-dose state has continued for a predetermined period of time or longer.

With this configuration, it is possible to automatically change from the high-dose state to the standard state. Therefore, it is possible to easily suppress the subject 101 from being continuously irradiated with a relatively high dose of X-rays in the high-dose state for a long period of time. Therefore, it is possible to effectively suppress the sum of doses of the X-rays emitted to the subject 101 from becoming excessive.

Modified Embodiments

It should be understood that the embodiments disclosed here are examples in all respects and are not restrictive. The scope of the present invention is shown by claims rather than the descriptions of the embodiments described above, and includes all changes (modifications) within the meaning of equivalent to claims.

For example, in the above-mentioned embodiment, an example is shown in which the dose change unit 73 (control unit 7) is configured to change the dose of X-rays to be emitted from the standard state to the high-dose state by relatively changing both the pulse rate, which is the number times of X-rays irradiations per unit time and the pulse dose, which is the dose of the X-rays emitted by one unit of irradiation, by a predetermined dose from the set standard state, but the present invention is not limited thereto. For example, it may be configured such that only the pulse rate is changeable by the dose change unit with the pulse dose not to be changeable. It is also possible to configure such that only the pulse dose is changeable by the dose change unit with the pulse rate not changeable.

In the above-described embodiment, an example is shown in which it is configured such that the preset setting unit 71 (control unit 7) presets the dose of X-rays to be emitted before performing the surgical operation while imaging the subject 101 and that the dose change unit 73 (control unit 7) changes the dose of X-rays to be emitted from the standard state to the high-dose state or the low-dose state, based on the input operation to the touch panel 6 (operation unit) during the surgical operation while imaging the subject 101, but the present invention is not limited thereto. For example, before the surgical operation, it may be configured such that the dose of X-rays to be emitted is changed from the standard state to the high-dose state or the low-dose state. Further, it may be configured such that the dose of X-rays to be emitted is set (the preset is changed) by the preset setting unit during the surgery (during the imaging).

In the above-described embodiment, an example is shown in which it is configured such that the preset setting unit 71 (control unit 7) sets the dose selected from the plurality of doses as a dose of X-rays to be emitted and that the dose change unit 73 (control unit 7) relatively changes the dose of X-rays to be emitted from the standard state to one of levels fewer than the levels of the plurality of doses, but the present invention is not limited thereto. For example, the number of levels settable by the dose setting unit may be the same as the number of selectable presets. In other words, it may be configured such that all of the doses (pulse rates and pulse doses) selectable as a preset can be set by the dose change unit.

In the above-described embodiment, an example is shown in which it is configured such that the dose change unit 73 (control unit 7) relatively changes the pulse dose from the standard state to the high-dose state in which the pulse dose is set to a level higher than the standard state by one level and to the low-dose state in which the pulse dose is set to a level lower than the standard state by one level, but the present invention is not limited thereto. For example, the high-dose state may be set to two or more levels in which the pulse dose is greater than that that in the standard state. Further, the low-dose state may be set to two or more levels in which the pulse dose is smaller than that in the standard state. In other words, it may be configured such that the pulse dose can be selected from three or more levels.

Further, in the above-described embodiment, an example is shown in which the apparatus is further provided with the touch panel 6 (display unit) capable of identifiably displaying the standard state, the high-dose state, and the low-dose state, but the present invention is not limited thereto. For example, it may be configured such that the standard state, the high-dose state, and the low-dose state are displayed in the image display unit in which the captured X-ray image is displayed in an identifiable manner. In this case, it may be configured such that the operation for changing from the standard state to the high-dose state or the low-dose state is accepted by a pointing device, such as, e.g., a keyboard and a mouse.

Further, in the above-described embodiment, an example is shown in which the apparatus is provided with the touch panel 6 including an operation unit and a display unit, but the present invention is not limited thereto. For example, the operation unit and the display unit may be configured separately.

In the above-described embodiment, the display control unit 74 (control unit 7) is configured to cause the touch panel 6 (display unit) to display the standard state, the high-dose state, and the low-dose state in a color-corded manner, but the present invention is not limited thereto. For example, the standard state, the high-dose state, and the low-dose state may be displayed in the same color. Alternatively, it may be configured such that the high-dose state and the low-dose state are displayed in an identifiable manner by displaying character information indicating the high-dose state and the low-dose state.

Further, in the above-described embodiment, an example is shown in which the touch panel 6 (operation unit) is provided at the top board 1, but the present invention is not limited thereto. For example, the touch panel 6 may be provided at a position spaced apart from the top board.

Further, in the above-described embodiment, an example is shown in which the apparatus is provided with the storage unit 8 for storing a plurality of doses (presets) set so as to correspond to the surgical operation performed on the subject 101, but the present invention is not limited thereto. For example, it may be configured such that the apparatus is not provided with the storage unit and the preset selected in advance before the imaging is set as a standard state by selecting the dose of X-rays to be emitted from a plurality of presets (doses) stored in an external storage unit.

Further, in the above-described embodiment, an example is shown in which it is configured such that the display control unit 74 (control unit 7) causes the touch panel 6 (display unit) to display an indication capable of identifying the dose (preset) preset by the preset setting unit 71, but the present invention is not limited thereto. For example, it may be configured such that the selected preset is not displayed.

Further, in the above embodiment, an example is shown in which the display control unit 74 (control unit 7) causes the touch panel 6 (display unit) to display an indication notifying that the X-ray irradiation in the high-dose state has continued for a certain period of time or longer when the X-ray irradiation in the high-dose state has continued for a certain period of time or longer, but the present invention is not limited thereto. For example, it may be configured such that a voice notification unit, such as a speaker, may be provided, or it may be configured to notify the fact that the X-ray irradiation in the high-dose state has continued for a predetermined period of time or longer may be notified by sound.

Further, in the above-described embodiment, an example is shown in which the dose change unit 73 (control unit 7) changes the dose of X-rays to be emitted to the standard state when the irradiation of X-rays in the high-dose state has continued for a certain period of time or more, but the present invention is not limited thereto. For example, it may be configured such that the sum value of the dose of the X-rays emitted to the subject is stored and the dose of X-rays to be emitted is changed to the standard state when it is determined that the total value of the dose of X-rays to be emitted by the time the surgical operation is completed (the imaging is completed) is larger than a predetermined value (e.g., 2Gy: gray).

Further, in the above-described embodiment, an example is shown in which when the X-ray irradiation in the high-dose state has continued for a predetermined period of time or longer, it is notified that the X-ray irradiation in the high-dose state has continued for a predetermined period of time or longer and that the dose of X-rays to be emitted is changed to the standard state, but the present invention is not limited thereto. For example, it may be configured such that the dose of X-rays to be emitted is automatically changed to the standard state when the X-ray irradiation in the high-dose state has continued for a certain period of time or longer. Further, it may be configured such that the dose of X-rays to be emitted is changed to the low-dose state when the X-ray irradiation in the high-dose state has continued for a predetermined period of time or longer.

Further, in the above-described embodiment, an example is shown in which the dose change unit 73 (control unit 7) changes the dose of X-rays irradiation from the standard state to the high-dose state or the low-dose state, but the present invention is not limited thereto. For example, it may be configured such that the dose change unit 73 changes the dose of X-rays to be emitted from the standard state only to the high-dose state and does not change the dose of X-rays to be emitted from the standard state to the low-dose state. Alternatively, it may be configured such that the dose change unit 73 changes the dose of X-rays to be emitted from the standard state only to the low-dose state and does not changes the dose of X-rays to be emitted from the standard state to the high-dose state.

Further, in the above-described embodiment, an example is shown in which the control unit 7 includes an FPGA, but the present invention is not limited thereto. For example, the control unit may include a computer including a CPU (Central Processing Unit), a GPU (Graphics Processing Unit), a ROM (Read Only Memory), and a RAM (Random Access Memory).

In the above-described embodiment, an example is shown in which the control unit 7 (FPGA) as one hardware includes, as software functional blocks, the preset setting unit 71, the standard state setting unit 72, the dose change unit 73, the display control unit 74, and the timer unit 75, but the present invention is not limited thereto. For example, two or more hardware may be composed of the preset setting unit 71, the standard state setting unit 72, the dose change unit 73, the display control unit 74, and the timer unit 75.

Further, in the above-described embodiment, an example is shown in which in the coronary intervention, the standard state is relatively changed to the high-dose state or the low-dose state, but the present invention is not limited thereto. For example, in a surgical form in which a stent is indwelled in a blood vessel of a head, a lower limb, or the like, other than a coronary artery of a heart, it may be configured to change from the standard state to the high-dose state or the low-dose state. Further, not in the case of performing a surgical form (surgical operation) for a blood vessel disease but in the case of performing X-ray fluoroscopy (X-ray TV imaging) of an internal organ such as a digestive organ, it may be configured to change from the standard state to the high-dose state or low-dose state.

Aspects

It will be understood by those skilled in the art that the above-described exemplary embodiments are concrete examples of the following aspects.

(Item 1)

A radiographic imaging apparatus for imaging an inside of a body of a subject by emitting X-rays to the subject from an X-ray irradiation unit including an X-ray tube, the radiographic imaging apparatus comprising:
  a control unit configured to control X-ray irradiation by the X-ray irradiation unit; and
  an operation unit configured to accept an operation for changing a dose of X-rays to be emitted,
  wherein the control unit includes:
  a preset setting unit configured to preset the dose of X-rays to be emitted;
  a standard state setting unit configured to set the dose of X-rays preset by the preset setting unit as a standard state; and
  a dose change unit configured to relatively change the dose of X-rays to be emitted with the standard state as a reference, based on an operation to the operation unit, from the standard state to at least one of a high-dose state in which the dose of X-rays to be emitted is higher than that in the standard state by a predetermined dose and a low-dose state in which the dose of X-rays to be emitted is lower than that in the standard state by the predetermined dose.

(Item 2)

The radiographic imaging apparatus as recited in the above-described Item 1, wherein the X-ray irradiation unit is configured to continuously emit X-rays to capture the image of the inside of the subject as a moving image, and wherein the dose change unit is configured to change the dose of X-rays to be emitted from the standard state to the high-dose state or the low-dose state, by relatively changing at least one of a pulse rate which is the number of times of X-ray irradiation per unit time and a pulse dose which is a dose of X-rays to be emitted by one X-ray irradiation, by a predetermined dose.

(Item 3)

The radiographic imaging apparatus as recited in the above-described Item 2, wherein the preset setting unit is configured to preset the dose of X-rays to be emitted before performing a surgical operation while imaging the subject, and wherein the dose change unit is configured to change the dose of X-rays to be emitted from the standard state to the high-dose state or the low-dose state, based on an input operation to the operation unit during the surgical operation is being performed while imaging the subject.

(Item 4)

The radiographic imaging apparatus as recited in the above-described Item 2 or 3, wherein the preset setting unit is configured to set the dose selected from a plurality of doses, as the dose of X-rays to be emitted, and wherein the dose change unit is configured to relatively change the dose of X-rays to be emitted from the standard state to one of levels whose number is fewer than the number of levels of the plurality of doses.

(Item 5)

The radiographic imaging apparatus as recited in the above-described Item 4, wherein the dose change unit is configured to relatively change the pulse dose from the standard state to the high-dose state in which the pulse dose is set to a level higher than the standard state by one level or the low-dose state in which the pulse dose is set to a level lower than the standard state by one level.

(Item 6)

The radiographic imaging apparatus as recited in any one of the above-described Items 2 to 5, further comprising:

a display unit configured to distinguishably display the standard state, the high-dose state, and the low-dose state, wherein the control unit includes a display control unit for causing the display unit to display a visually identifiable indication on whether or not each of the pulse rate and the pulse dose has been changed from the standard state.

(Item 7)

The radiographic imaging apparatus as recited in the above-described Item 6, wherein the display control unit is configured to cause the display unit to display the standard state, the high-dose state, and the low-dose state in a color-coded manner.

(Item 8)

The radiographic imaging apparatus as recited in the above-described Item 6 or 7, further comprising;

a top board configured for the subject to lie down thereon, wherein the operation unit is provided at the top board and includes a button for changing the pulse rate and a button for changing the pulse dose.

(Item 9)

The radiographic imaging apparatus as recited in any one of the above-described Items 6 to 8, further comprising;

a storage unit configured to store a plurality of doses set to correspond to a surgical operation to be performed on the subject, wherein the standard state setting unit is configured to set the dose preset by the preset setting unit before imaging from a plurality of doses stored in the storage unit, as the standard state, and wherein the display control unit is configured to cause the display unit to display an indication capable of identifying the dose preset by the preset setting unit.

(Item 10)

The radiographic imaging apparatus as recited in any one of the above-described Items 6 to 9, wherein the display control unit is configured to cause the display unit to display an indication notifying that the X-ray irradiation in the high-dose state has continued for a predetermined period of time or longer when the X-ray irradiation in the high-dose state has continued for a predetermined period of time or longer.

(Item 11)

The radiographic imaging apparatus as recited in any one of the above-described Items 1 to 10 wherein the dose change unit is configured to change the dose of X-rays to be emitted to the standard state when the X-ray irradiation in the high-dose state has continued for a predetermined period of time or longer.

The invention claimed is:

1. A radiographic imaging apparatus for imaging an inside of a body of a subject by emitting X-rays to the subject from an X-ray irradiation unit including an X-ray tube, the radiographic imaging apparatus comprising:

a control unit configured to control X-ray irradiation by the X-ray irradiation unit; and an operation unit configured to accept an operation for changing a dose of X-rays to be emitted, wherein the control unit includes:

a preset setting unit configured to preset the dose of X-rays to be emitted;

a standard state setting unit configured to set the dose of X-rays preset by the preset setting unit as a standard state; and a dose change unit configured to relatively change the dose of X-rays to be emitted with the standard state as a reference, based on an operation to the operation unit, from the standard state to at least one of a high-dose state in which the dose of X-rays to be emitted is higher than that in the standard state by a predetermined dose and a low-dose state in which the dose of X-rays to be emitted is lower than that in the standard state by the predetermined dose.

2. The radiographic imaging apparatus as recited in claim 1, wherein the X-ray irradiation unit is configured to continuously emit X-rays to capture the image of the inside of the subject as a moving image, and wherein the dose change unit is configured to change the dose of X-rays to be emitted from the standard state to the high-dose state or the low-dose state, by relatively changing at least one of a pulse rate which is the number of times of X-ray irradiation per unit time and a pulse dose which is a dose of X-rays to be emitted by one X-ray irradiation, by a predetermined dose.

3. The radiographic imaging apparatus as recited in claim 2,
wherein the preset setting unit is configured to preset the dose of X-rays to be emitted before performing a surgical operation while imaging the subject, and
wherein the dose change unit is configured to change the dose of X-rays to be emitted from the standard state to the high-dose state or the low-dose state, based on an input operation to the operation unit during the surgical operation is being performed while imaging the subject.

4. The radiographic imaging apparatus as recited in claim 2,
wherein the preset setting unit is configured to set the dose selected from a plurality of doses, as the dose of X-rays to be emitted, and
wherein the dose change unit is configured to relatively change the dose of X-rays to be emitted from the standard state to one of levels whose number is fewer than the number of levels of the plurality of doses.

5. The radiographic imaging apparatus as recited in claim 4,
wherein the dose change unit is configured to relatively change the pulse dose from the standard state to the high-dose state in which the pulse dose is set to a level higher than the standard state by one level or the low-dose state in which the pulse dose is set to a level lower than the standard state by one level.

6. The radiographic imaging apparatus as recited in claim 2, further comprising:
a display unit configured to distinguishably display the standard state, the high-dose state, and the low-dose state,
wherein the control unit includes a display control unit for causing the display unit to display a visually identifiable indication on whether or not each of the pulse rate and the pulse dose has been changed from the standard state.

7. The radiographic imaging apparatus as recited in claim 6,
wherein the display control unit is configured to cause the display unit to display the standard state, the high-dose state, and the low-dose state in a color-coded manner.

8. The radiographic imaging apparatus as recited in claim 6, further comprising;
a top board configured for the subject to lie down thereon,
wherein the operation unit is provided at the top board and includes a button for changing the pulse rate and a button for changing the pulse dose.

9. The radiographic imaging apparatus as recited in claim 6, further comprising:
a storage unit configured to store a plurality of doses set to correspond to a surgical operation to be performed on the subject,
wherein the standard state setting unit is configured to set the dose preset by the preset setting unit before imaging from a plurality of doses stored in the storage unit, as the standard state, and
wherein the display control unit is configured to cause the display unit to display an indication capable of identifying the dose preset by the preset setting unit.

10. The radiographic imaging apparatus as recited in claim 6,
wherein the display control unit is configured to cause the display unit to display an indication notifying that the X-ray irradiation in the high-dose state has continued for a predetermined period of time or longer when the X-ray irradiation in the high-dose state has continued for a predetermined period of time or longer.

11. The radiographic imaging apparatus as recited in claim 1,
wherein the dose change unit is configured to change the dose of X-rays to be emitted to the standard state when the X-ray irradiation in the high-dose state has continued for a predetermined period of time or longer.

* * * * *